Figure 4:
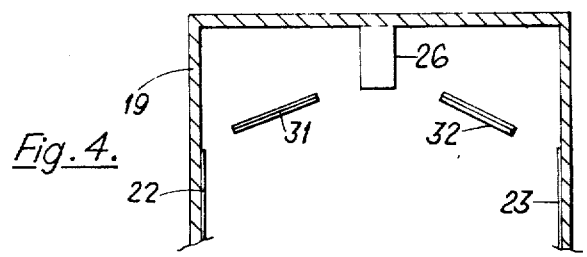

United States Patent [19]
Clarke

[11] 3,931,525
[45] Jan. 6, 1976

[54] DETECTION OF BLEMISHES IN SURFACES

[75] Inventor: Graham Morley Clarke, Edinburgh, Scotland

[73] Assignee: Ferranti, Limited, Hollinwood, England

[22] Filed: Sept. 7, 1973

[21] Appl. No.: 394,980

[30] Foreign Application Priority Data
Sept. 21, 1972 United Kingdom............ 43838/72

[52] U.S. Cl. ............... 250/572; 250/216; 356/200
[51] Int. Cl.² ...................................... G01N 21/32
[58] Field of Search .......... 250/562, 563, 572, 216, 250/236; 356/200, 237, 201, 239

[56] References Cited
UNITED STATES PATENTS

| | | | |
|---|---|---|---|
| 2,806,401 | 9/1957 | Demuth et al. | 356/237 |
| 3,061,731 | 10/1962 | Thier et al. | 250/563 |
| 3,396,281 | 8/1968 | Blackman | 250/239 |
| 3,549,264 | 12/1970 | Christie | 356/210 |
| 3,572,947 | 3/1971 | Sepall | 356/239 X |
| 3,675,016 | 7/1972 | Blaisdell et al. | 250/236 X |
| 3,723,747 | 3/1973 | Steele | 250/239 X |

Primary Examiner—Walter Stolwein
Attorney, Agent, or Firm—Cameron, Kerkam, Sutton, Stowell & Stowell

[57] ABSTRACT

A detector of blemishes in a surface comprises a transmitting station from which a beam of light is caused to scan a moving surface to produce a raster pattern thereon. Light specularly reflected from, or transmitted by, the surface is collected at a receiving station after being diffused by a sheet of translucent material disposed in the path of this light. The diffused light in the receiving station is collected and directed by reflective surfaces towards a photodetector such that when the beam engages a blemish in the surface, the amount of light detected falls. The detector combines the sensitivity of collecting large amounts of specularly reflected light with a simple optical system associated with the collecting of diffused light.

10 Claims, 8 Drawing Figures

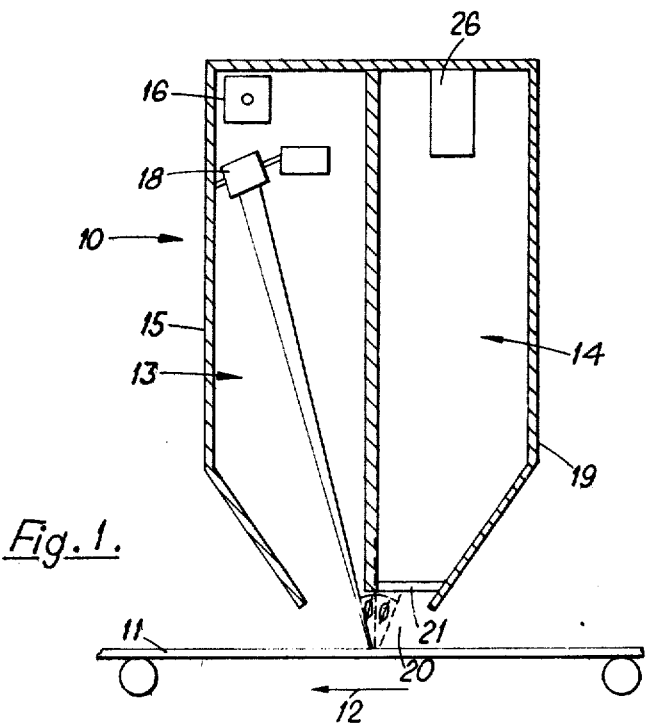
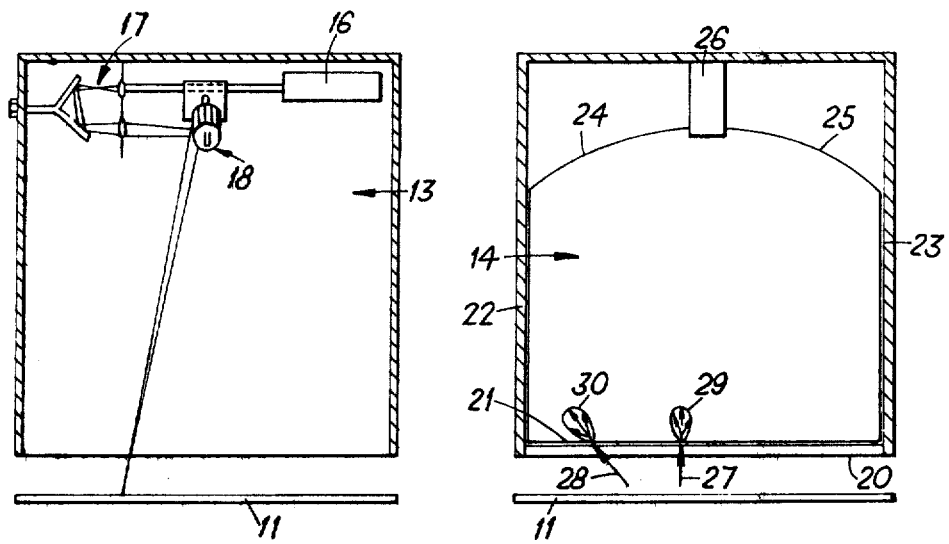
Fig. 1.
Fig. 2.
Fig. 3.

DETECTION OF BLEMISHES IN SURFACES

This invention relates to the detection of blemishes in surfaces.

Detectors of blemishes in surfaces are known and particularly detectors of blemishes in the surface of moving webs. In such detectors a beam of light is brought to a focus at the surface of the moving web and is scanned over the surface repetitively and transversely to the direction of motion of the web. Light reflected from, or transmitted by, the surface is collected in a receiver and any change in its intensity, caused by a blemish in the surface, is detected and counted.

Reflected light has a component due to specular reflection and a component due to diffuse reflection, and the proportion of either component is dependent on the nature of the surface. For detecting diffusely reflected light a photo-detector has to make a collection of most of the available diffusely reflected light and requires only a simple optical arrangement, although the light is collected at a low level of intensity. Because of this low-level working, steps must be taken to prevent any high intensity specularly reflected light from being collected. Specularly reflected light, while being of high intensity at the specular angle, and therefore desirable to be collected in a blemish detector, is difficult to collect completely because of the continuous variation of the specular angle throughout the scan. Known receivers of specularly reflected light require complex optical arrangements but are generally of high sensitivity. Similar considerations apply to light transmitted by a surface.

It is an object of the present invention to provide a detector of blemishes in a surface, which detector is of simple optical construction.

According to the present invention a detector of blemishes in a surface comprises a scanning station, the detector and surface being movable relative to one another, the detector including a transmitting station comprising a source of a beam of electromagnetic radiation and scanning means operable to cause the beam to scan the surface transversely to the direction of said relative motion and a receiving station comprising radiation diffusing means disposed so as to intercept radiation specularly reflected from the surface and radiation detection means responsive to a reduction in the level of the radiation diffused by said diffusing means to provide an output signal indicative of the engagement of a blemish by the beam.

Figure 5:
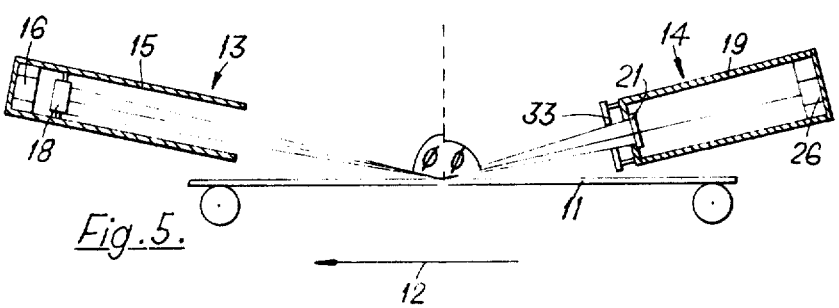
Figure 6:
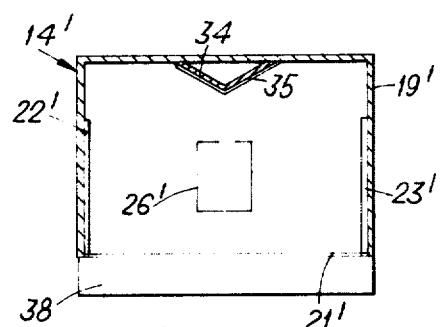
Figure 7:
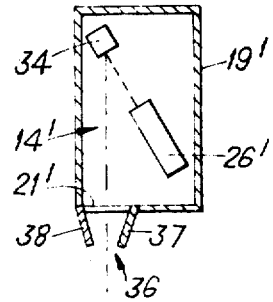
Figure 8:
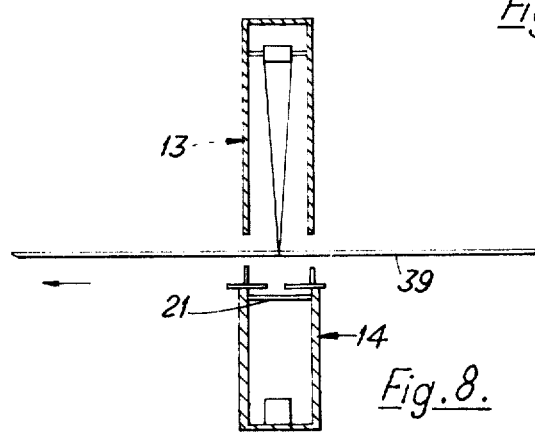

The invention will now be described by way of example with reference to the accompanying drawings, in which:

FIG. 1 is a sectional end elevation of a blemish detector according to the present invention, FIG. 2 is a sectional elevation of the transmitting station of the detector of FIG. 1, FIG. 3 is a sectional elevation of the receiving station of the detector of FIG. 1, FIG. 4 is a sectional elevation showing an alternative form of the receiving station of FIG. 3, FIG. 5 is a sectional end elevation of an alternative arrangement of the blemish detector of FIG. 1, FIGS. 6 and 7 are sectional end and side elevations respectively of a modified form of receiving station, and FIG. 8 is a further alternative arrangement of the blemish detector of FIG. 1 for use with a transmissive surface.

Referring to FIG. 1 there is shown a blemish detector 10 adjacent to a surface 11 of a web of material caused to move past the blemish detector in the direction of the arrow 12.

The detector 10 comprises two adjacent stations 13 and 14 both extending across the width of the web. The station 13, and also shown in FIG. 2, is a transmitting station. This comprises an enclosure 15, a laser 16, an optical system 17 and a rotatable multifaceted mirror 18.

In operation light, emitted in a continuous beam by the laser 16, is brought to a focus at the surface 11 by the optical system 17 and after reflection from the mirror 18. The mirror 18 is caused to rotate at a high speed and as each facet of the mirror passes through the beam, the beam is caused to scan across the web from side to side. The axis of rotation of the mirror 18 is inclined to the plane of the surface 11 such that the beam approaches the surface 11 at an incident angle $\theta$ to the normal to the plane.

Depending on the surface, radiation is reflected or transmitted, but the following description relates to reflection only.

Depending upon the nature of the reflective surface, light is to some extent specularly and diffusely reflected. For instance, steel and glazed paper produce mainly a specular reflection with some diffuse reflection, whereas coarse paper and cloth produce mainly diffuse reflection with some specular reflection. The detector of the present invention is primarily intended for use with surfaces of the first mentioned type.

Referring also to FIG. 3, there is shown a light receiving station 14 which is particularly suited to receive light specularly reflected from the surface. This comprises an enclosure 19, similar to that of the transmitting station and also extending across the width of the surface 11 (which moves into the plane of the drawing). Light is only able to enter the enclosure 19 by way of an opening 20 extending across the bottom of the enclosure adjacent the surface 11. The opening 20 is occupied by a light diffuser 21 parallel to the surface 11. The end walls 22 and 23 of the enclosure have mirrored surfaces and the upper portion of the enclosure has curved reflecting surfaces 24 and 25. The photodetector 26 is mounted at the centre of the curved wall opposite to the diffuser 21.

Light from the laser 16, incident on the surface at said angle $\theta$ to the normal and specularly reflected from the surface, travels also at angle $\theta$ to the normal towards the diffuser 21 through which it passes to the enclosure in a diffused form. The diffused light is collected by the photodetector 26 which gives an output signal in dependence on the amount of light collected. Ideally the diffused light is completely non-directional but in practice light passing through the diffuser at an oblique angle retains some directivity. In FIG. 3 the response of the diffuser 21 to beams 27 and 28 is shown in terms of polar diagrams 29 and 30 respectively. The beam 27 approaching the diffuser normally is diffused by transmission but with the greatest portion of the light continuing in the same general direction towards the photo detector 26. The beam 28 approaching the diffuser 21 at an oblique angle is diffused by transmission with the greatest portion of the diffused light continuing in the same direction and not towards the photodetector; the reflecting wall 22 directs the light towards the photodetector and compensates for a reduction in light level towards the end of the scan that would result if the wall 22 absorbed the light reaching it. The curved surfaces 24 and 25 between the end walls and the photodetector compensate for variations in the amount of light reaching the photodetector throughout the scan.

The reflecting end walls 22 and 23 and the curved surfaces 24 and 25 approximate to the conic-section reflector that would be required to direct a non-diffused beam towards the photodetector. However, the system requires no great optical accuracy and the curved surfaces 24 and 25 may be adequately replaced by plane mirrors 31 and 32 as shown in FIG. 4. The plane mirrors 31 and 32 are advantageous as the inclination of the mirrors may be changed to suit the reflective characteristics of the surface being scanned.

Referring to FIG. 5 there is shown an alternative arrangement of the blemish detector wherein the transmitting station and the receiving station are widely separated. The transmitting station is inclined at a large angle $\phi$ to the normal to the surface and the receiving station is inclined also at an angle $\phi$ to the normal, on the other side of the normal, in a plane parallel to the direction of movement of the surface 11. The light diffuser 21 is now disposed so as to be struck normally by the beam after reflection at the surface.

To decrease the amount of diffusely reflected light received by the photodetector in relation to light specularly reflected, a slit element 33 may be placed in the path of the reflected light adjacent the light diffuser 21. Such a slit increases the sensitivity of the blemish detector to local deformations of the surface which are not accompanied by changes in reflectivity. The use of such a slit is subject to the arrangement employing it not being too sensitive to surface flatness, because the surface may not be held steady during transport past the blemish detector.

In the receiving stations described above the reflecting arrangements have corresponded to a conic section with the photodetector at the focus but of the crude geometrical form permitted by the use of the diffuser. Referring to FIGS. 6 and 7 there is shown a more compact form of receiving station 14'. The station comprises an enclosure 19' containing a photodetector 26' and a diffuser 21'. The photodetector 26' is directed away from the diffuser 21' towards mirrors 34 and 35 inclined so as to direct light reflected from end walls 22' and 23' towards the photodetector. In this way the intensity of light in the envelope and directed towards the photodetector is uniform throughout the scan. Also because the light paths are 'folded' the overall height of the receiving station may be reduced; this is particularly advantageous in the case of physically separated transmitting and receiving stations. The diffuser 21' is shielded from ambient light by a hood 36. The hood may comprise hinged flaps 37 and 38, which flaps may be positioned so as to provide the effect of the slit element 33 shown in FIG. 5.

Thus the blemish detector combines the simple light collection optics associated with the collection of diffusely reflected light while having the sensitivity associated with the intensity of specularly reflected light.

The light source may comprise a non-coherent lamp — such as a xenon lamp or a source operating outside of the visible part of the spectrum, that is, in the near infra-red or near ultra-violet, depending on the surface.

The detector of blemishes has been described with reference to a surface which is totally reflecting of incident radiation. Some surfaces are transmissive of radiation while others are capable of transmitting or reflecting radiation in dependence on the angle of incidence of the beam. Referring to FIG. 8 there is shown a sectional end view of a transmitting station 13 and a receiving station 14, the stations being on opposite sides of a transparent web 39. Visible radiation from the transmitting station scans the surface in a beam and in the absence of a blemish passes through the web and enters the receiving station by way of the diffuser 21. Diffused light is collected and detected in the usual way until a blemish prevents the surface from transmitting it. The detection means distinguishes the reduction in light and indicates the presence of a blemish. The transmitting station 13 may be inclined at an angle to the surface but account must then be taken of the refractive properties of the material in determining the position of the receiving station.

What I claim is:

1. A detector of blemishes in a surface, the detector and surface being movable relative to one another, the detector including a transmitting station comprising a source of a beam of electromagnetic radiation, focussing means operable to focus the beam to a spot at the surface, the spot having an area of the same order of magnitude as the smallest blemish to be detected, and scanning means operable to cause the beam to scan the surface transversely to the direction of said relative motion, and a receiving station comprising radiation detection means inside a light integrating enclosure having an aperture extending across the width of the scan to collect light substantially only specularly reflected from said surface, and diffusing means mounted in, and coextensive with, said aperture, and through which said reflected light passes, the radiation detection means being responsive to a reduction in the level of diffused light in the enclosure to provide an indication of a blemish at the corresponding position of the beam.

2. A detector of blemishes as claimed in claim 1 in which the radiation diffusing means is disposed so as to intercept that portion of the beam specularly reflected from the surface.

3. A detector of blemishes as claimed in claim 2 in which the transmitting and receiving stations are located adjacent each other.

4. A detector of blemishes as claimed in claim 1 in which the source of the beam of radiation is a laser.

5. A detector of blemishes as claimed in claim 1 in which the radiation is in the visible part of the electromagnetic spectrum.

6. A detector of blemishes as claimed in claim 5 in which the radiation diffusing means comprises a sheet of translucent material arranged to extend substantially normally to the plane of the beam emanating from the surface.

7. A detector of blemishes as claimed in claim 1 in which the enclosure containing the detection means comprises side walls which extend along opposite sides of said diffusing means and generally parallel to the direction of scan of the beam, and end walls entending between said side walls at each end of the diffusing means and generally perpendicular to the direction of scan of the beam, said end walls having internal surfaces arranged to reflect diffused radiation incident thereupon towards said detection means.

8. A detector of blemishes as claimed in claim 7 in which the detection means is arranged within the enclosure so as to receive only radiation reflected from said end walls.

9. A detector of blemishes as claimed in claim 7 in which the enclosure contains further radiation reflective surfaces, disposed between said end walls and said detection means, arranged so as to direct radiation incident thereon towards the detection means.

10. A detector of blemishes as claimed in claim 9 in which said further reflective surfaces comprise parts of a conic section, said detection means being arranged substantially at the focus of the section.

* * * * *